US011369130B2

(12) United States Patent
Mabee et al.

(10) Patent No.: US 11,369,130 B2
(45) Date of Patent: Jun. 28, 2022

(54) VAPORIZER APPARATUS TO PRODUCE VAPOR WITHOUT THE USE OF A HEAT SOURCE

(71) Applicant: MABEE ENGINEERED SOLUTIONS, INC., Shelby Township, MI (US)

(72) Inventors: Brian D. Mabee, Shelby Township, MI (US); Kathryn Mabee, Shelby Township, MI (US); Austin M. Mabee, Shelby Township, MI (US); Marc Longfellow, Ponce Inlet, FL (US)

(73) Assignee: Mabee Engineered Solutions, Inc., Shelby Township, MI (US)

( * ) Notice: Subject to any disclaimer, the term of this patent is extended or adjusted under 35 U.S.C. 154(b) by 487 days.

(21) Appl. No.: 16/549,241

(22) Filed: Aug. 23, 2019

(65) Prior Publication Data

US 2021/0052016 A1 Feb. 25, 2021

(51) Int. Cl.

| | |
|---|---|
| ***A24F 13/00*** | (2006.01) |
| ***A24F 17/00*** | (2006.01) |
| ***A24F 25/00*** | (2006.01) |
| ***A24B 15/167*** | (2020.01) |
| ***A61M 11/04*** | (2006.01) |

(52) U.S. Cl.

CPC ......... *A24B 15/167* (2016.11); *A61M 11/042* (2014.02); *A61M 2205/8206* (2013.01)

(58) Field of Classification Search

CPC .......... A24F 40/10; A24F 40/48; A24F 40/05; A24F 40/485; A24F 40/51; A24F 7/00; A61M 11/042; A61M 2205/8206; F04B 35/04; F04B 37/06; F04B 37/14; F04B 37/20; F04B 45/047

See application file for complete search history.

(56) References Cited

U.S. PATENT DOCUMENTS

| | | | | |
|---|---|---|---|---|
| 2014/0251330 | A1* | 9/2014 | Collins ............ | A61M 15/0021 128/203.14 |
| 2018/0199627 | A1* | 7/2018 | Bowen .................. | A24F 40/485 |
| 2020/0289770 | A1* | 9/2020 | Hebrank ............... | A61M 15/08 |
| 2020/0330706 | A1* | 10/2020 | Greenfield ........... | A61M 15/06 |

* cited by examiner

*Primary Examiner* — Abdullah A Riyami
*Assistant Examiner* — Thang H Nguyen
(74) *Attorney, Agent, or Firm* — Carrier Blackman & Associates, P.C.; Joseph P. Carrier; William D. Blackman

(57) ABSTRACT

A handheld, portable vaporizer apparatus is operable to vaporize oils, such as e-liquids, cannabis oils, or dry herbs, without heating the oils. The vaporizer apparatus includes a main housing having an oil chamber, an oil reservoir connected to the oil chamber, and an evacuation chamber connected to the oil reservoir formed therein; an operation unit; a manifold connected to the main housing; a pump; and a control unit connected to the operation unit and pump. When the operation unit is operated, the oil reservoir is isolated from the oil chamber and the bottom of the evacuation chamber is sealed thereby creating a vacuum sealed chamber having oil trapped therein and being connected with an inlet of the pump, and the control unit turns the pump on causing a pressure differential so that oil trapped in the vacuum sealed chamber vaporizes without heat and flows through the manifold and mouthpiece.

20 Claims, 17 Drawing Sheets

10 Tf Tf Tp Tf Tf 24 26 21 22, 22a U1 28 V1 50 BC U2 A1 A2 84 80 14 38 A3 A4 B1 82 72b 74b 79 Bf Bf 20 C2 C1 64 Bp G1 G2 V2 Bf B3 F1 77 B4 70 42 F2 F3 90 C4 B2 F4 C3 78

20
50
80
30
70
90

VAPORIZER APPARATUS TO PRODUCE VAPOR WITHOUT THE USE OF A HEAT SOURCE

BACKGROUND OF THE INVENTION

1. Field of the Invention

The present invention relates to a handheld vaporizer apparatus that vaporizes oils or liquids, such as e-liquids, cannabis oil or dry herbs at or below room temperature. More particularly, the present invention relates to a handheld vaporizer apparatus that is operable to vaporize oil at or below room temperature, or at a desired temperature without subjecting the oils or liquids to a heat source or heating element, but rather by greatly reducing the pressure of the oils or liquids.

2. Description of Related Art

There are several known vaporizers that vaporize liquid substance. The liquid substance includes e-liquids (commonly referred to as a juice), cannabis oil (Cannabidiol (CBD) oil) and Tetrahydrocannabinol ((THC) oil), essential oils, or dry herbs. The vaporizer apparatuses are sometimes referred to as vaporizers, electronic cigarettes, vaping device and vape devices. The liquid substance is stored in a device, such as anatomizer, cartomizer, or clearomizer, which is screwed on to the vaporizer apparatus and is used to deliver the liquid into vapor form when heated. A typical vaporizer apparatus includes an oil chamber or device for storing oil, a heating element, e.g., a heating coil, a battery which powers the heating coil, and an activation switch or other mechanism for activating the heating coil, which converts the liquid substance to a vapor form, with a mouthpiece that is used by a user to inhale the vapor.

The existing vaporizer apparatuses are disadvantageous in that the existing vaporizer apparatuses use a heating element (e.g., a heating coil) for heating and thereby subsequently vaporize the oil at a temperature of vapor that may not be controlled. In some instances, there is a risk of inhaling vapor nearing a combustion temperature, which may injure a person's throat using the vaporizer apparatus due to a harsh or hot vapor. The temperature of the heating coil used in some vaporizer apparatuses may range from 110° C. to 1000° C. depending on wick condition, e.g., dry, wet-through-wick, and full-wet conditions of the vaporizer apparatus. It is also possible that heating the oil may alter composition of vapor, specifically, if heated at a high temperature.

The present invention has been made to overcome the drawbacks of the existing vaporizers. Accordingly, it is one of the objects of the present to provide a vaporizer apparatus configured to produce vapor from the oil or liquid at or below room temperature without the use of a heat source or heating element.

SUMMARY OF THE INVENTION

The present invention according one aspect thereof provides a vaporizer apparatus that can produce vapors from the liquid substance at or below room temperature. The vaporizer apparatus includes a first housing, configured to receive a battery holder and a control unit, including a circuit board, with the battery holder being adaptable to receive a battery (power source) therein; a hall effect sensor attached to the circuit board; a main housing connected to the first housing, the main housing having an oil chamber, an oil reservoir and an evacuation chamber formed therein, the oil reservoir being formed between the oil chamber and the evacuation chamber; an operation unit mounted onto the main housing, with the operation unit including a plurality of seals operable to selectively isolate the oil reservoir and the evacuation chamber from the oil chamber, and a magnetic nut which operatively connects with the hall effect sensor or an activation switch or other mechanism which is connected to the circuit board of the control unit, with the oil reservoir and the evacuation chamber forming a vacuum sealed chamber when isolated from the oil chamber; a manifold connected to the main housing, the manifold including a first compartment and a second compartment separate from the first compartment, the first compartment being connected to the vacuum sealed chamber; a piezo pump operatively connected to the battery or a power source, and attached to the manifold, the piezo pump having an inlet opening connected to the first compartment of the manifold, and an outlet opening connected to the second compartment of the manifold; and a mouthpiece connected to the second compartment of the manifold. The hall effect sensor may be replaced by a switch or any other mechanism, such as simply sucking and/or inhaling on a mouthpiece by an user. The manifold and the pump may be combined into a single housing to reduce part count.

The present invention according to another aspect thereof, in addition to the above aspect, is characterized in that when the operation unit is operated, the evacuation chamber and the oil reservoir are isolated from the oil chamber thereby creating the vacuum sealed chamber and causing the movement of the magnetic nut to reach a point that triggers the hall effect sensor or an activation switch or other mechanism, which provides a signal to the control unit to switch the piezo pump on. The operation of the piezo pump reduces pressure in the vacuum-sealed chamber, causing vaporization of the oil at or below a room temperature.

It may be noted that the oil is not subjected to a heating element or a heat source for vaporization thereof. Rather, the vaporization of the liquid substance occurs due to subjecting the oil to a very low pressure.

For a more complete understanding of the present invention, the reader is referred to the following, non-limiting, detailed description section, which describes an exemplary embodiment of the present invention and should be read in conjunction with the accompanying drawings. Such exemplary embodiment is provided for illustration and better understanding of the present invention and is not intended to limit the invention. Throughout the following detailed description and in the drawings, like numbers refer to like parts.

DETAILED DESCRIPTION OF ILLUSTRATIVE EMBODIMENTS

Illustrative embodiments of vaporizer apparatus according to the present invention will now be described hereinafter in detail with reference to the accompanying drawings. Throughout this description, relative terms like "top", "bottom", "back", "from", "left", "right", and the like are used in reference to a vantage point of an user of the vaporizer apparatus. It should be understood that these terms are used for purposes of illustration, and are not intended to limit the invention.

The vaporizer apparatus of the present invention may alternatively be referred to as electronic cigarette, vaping device, and vape device.

First Embodiment

Figure 1:
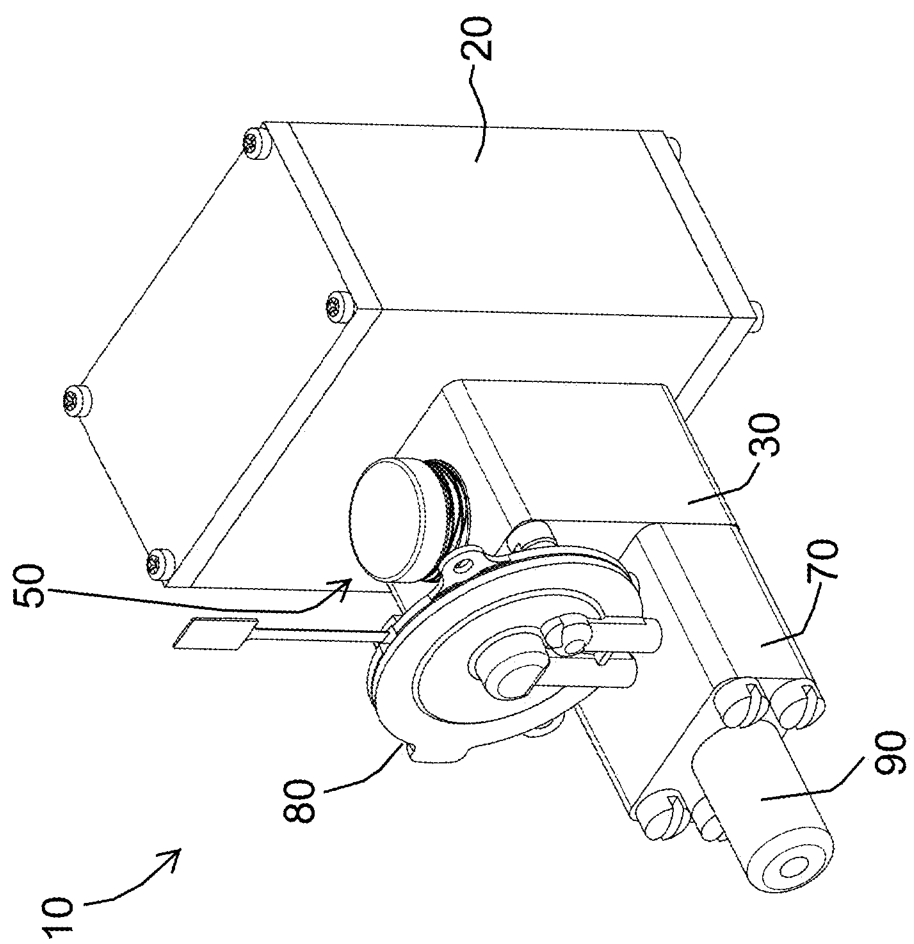
FIG. 1 shows a perspective view of a vaporizer apparatus as viewed from right front top according to the first embodiment of the present invention.

A vaporizer apparatus 10 according to first embodiments of the present invention is shown in FIGS. 1-9. FIG. 1 is a perspective view of the vaporizer apparatus 10 as viewed from right front top according the first embodiment of the present invention.

As shown in FIG. 1, the vaporizer apparatus 10 generally includes a first housing (also referred to as a battery/circuit board housing) 20, a main housing (also referred to as a housing) 30 connected to the first housing 20, an operation unit 50 mounted into the main housing 30, a manifold 70 (also referred to as an air flow chamber) connected to the main housing 30, a pump 80 connected to the manifold 70, and a mouthpiece 90 connected to the manifold 70. The pump 80 used in the present invention may be a piezo electric pump, a micro piezo electric pump, a piezoelectric diaphragm micropump, or any other type of pump. The manifold 70 and the pump 80 may be combined into a single housing to reduce part count, or may be integrally formed as one unit. The pump 80 may be entirely concealed within the manifold 70.

It may be noted that the first housing 20, the main housing 30, the manifold 70 and the mouthpiece 90 of the vaporizer apparatus 10 are arranged in series and are connected in this order. As it can be seen from FIG. 2, the vaporizer apparatus 10 of the present invention has a modular structure. In other words, the vaporizer apparatus 10 includes several units, i.e., the first housing 20, the main housing 30, the operation unit 50, manifold 70, the mouthpiece 90, which are formed as individual units. However, the first housing 20, the main housing 30, manifold 70, and the mouthpiece 90 may be integrally formed as one unit structure.

Figure 2:
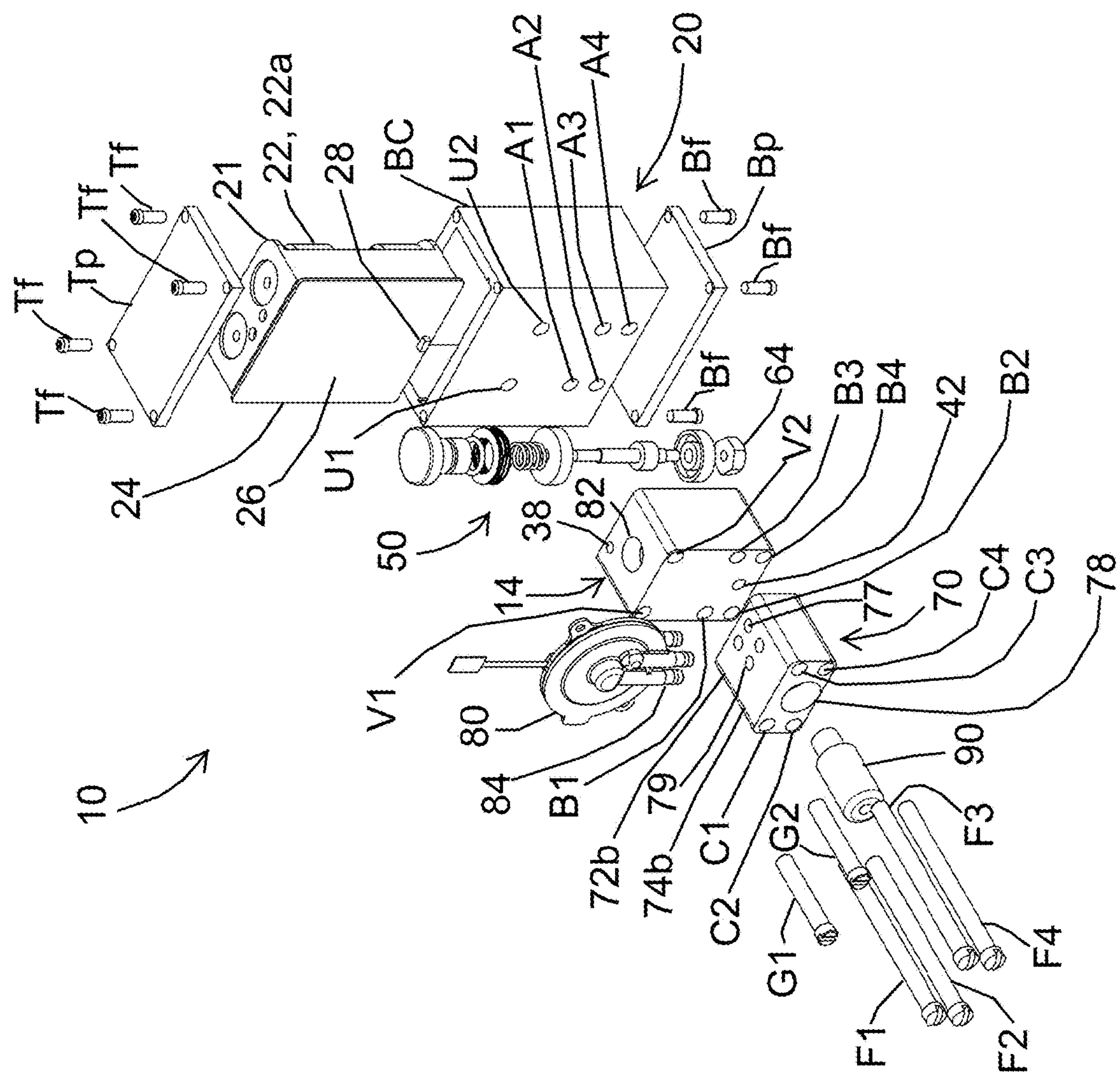
FIG. 2 shows an exploded view of the vaporizer apparatus as viewed from right front top according to the first embodiment.
Figure 3:
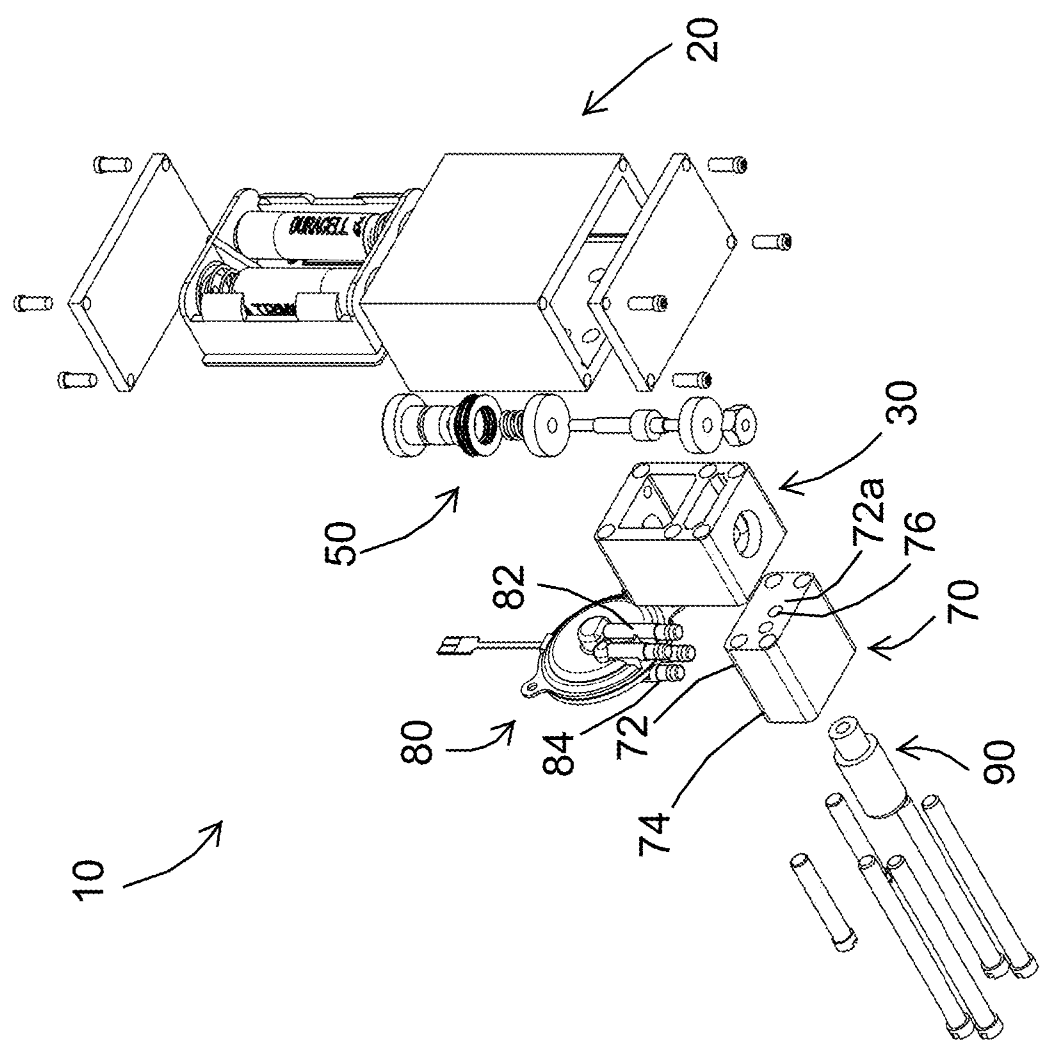
FIG. 3 shows another exploded view of the vaporizer apparatus as viewed from right bottom back according to the first embodiment.
Figure 4:
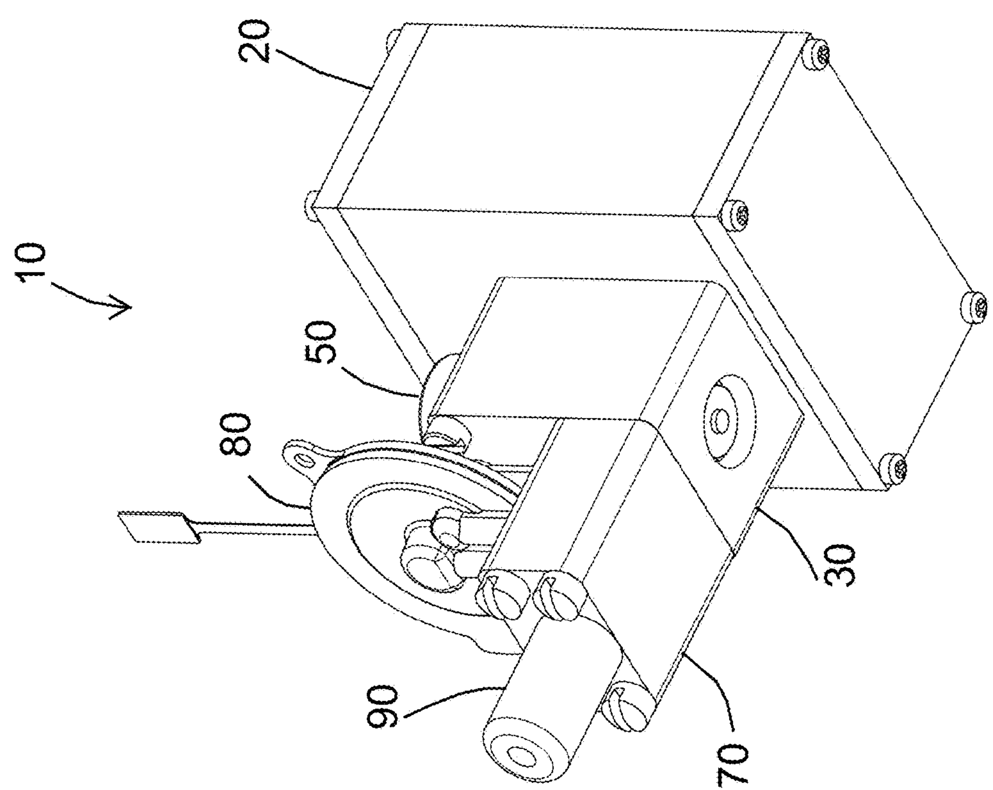
FIG. 4 shows a perspective view of the vaporizer apparatus as viewed from right front bottom according to the first embodiment.
Figure 5:
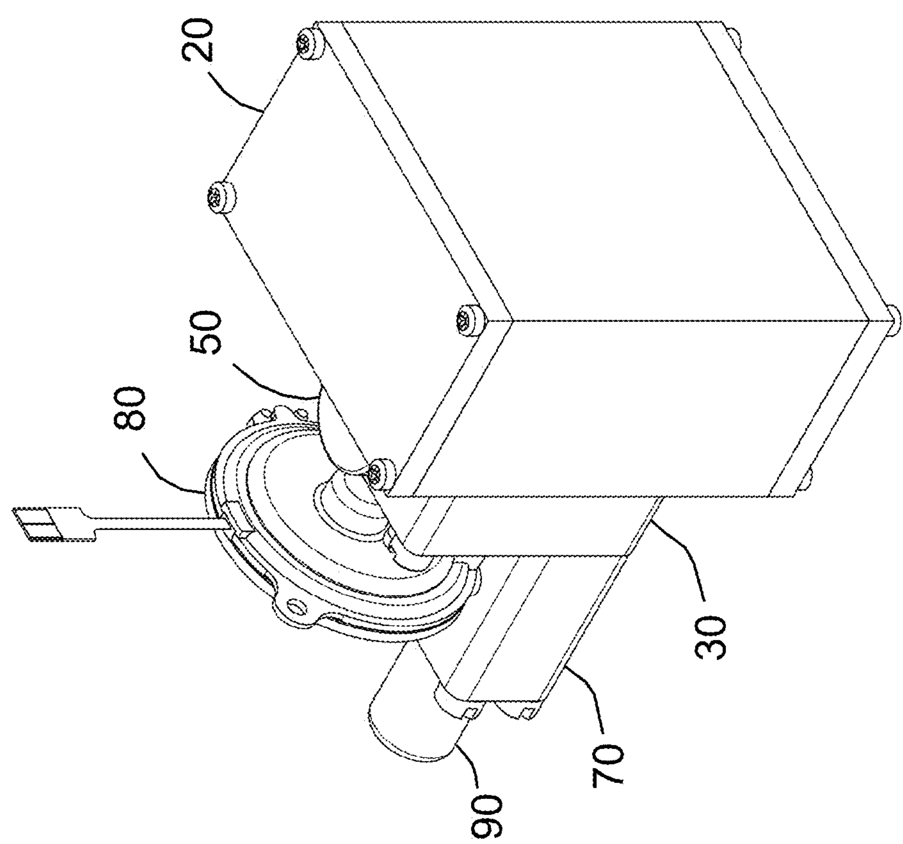
FIG. 5 shows a perspective view of the vaporizer apparatus as viewed from right back top according to the first embodiment.
Figure 6:
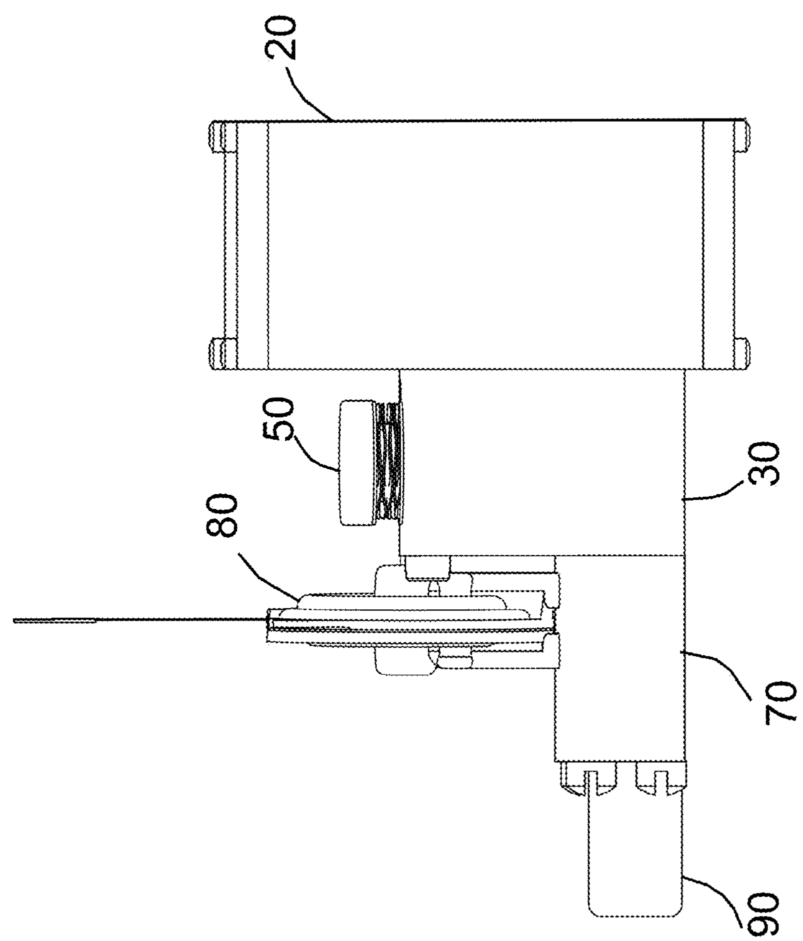
FIG. 6 shows a right side view of the vaporizer apparatus according to the first embodiment.
Figure 7:
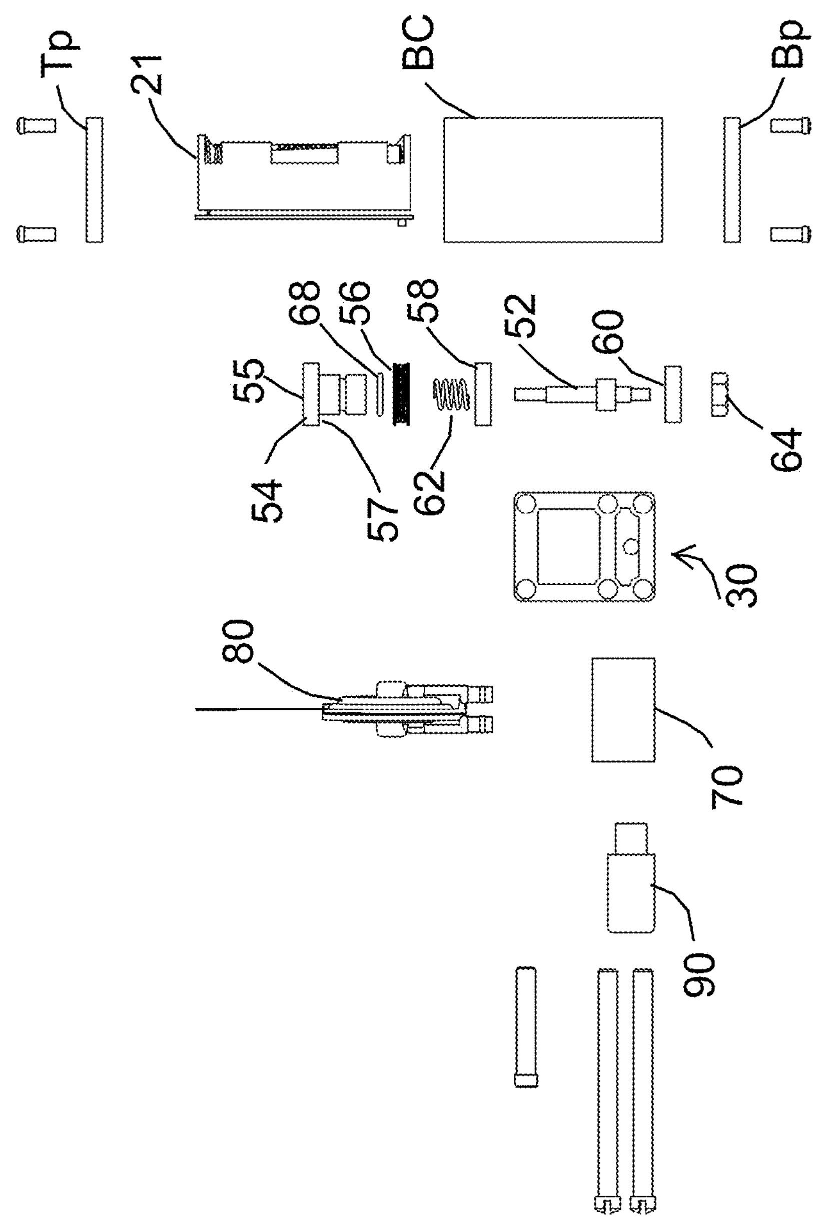
FIG. 7 shows an exploded view of the vaporizer apparatus as viewed right side according to the first embodiment.
Figure 8:
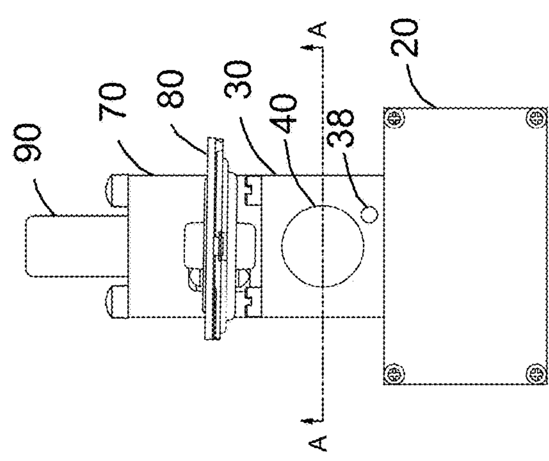
FIG. 8 is a sectional view of the vaporizer apparatus according to the first embodiment.

As shown in FIG. 2, the first housing 20 has connecting holes A1, A2, A3, A4 formed therein. The main housing 30 has connecting holes B1, B2, B4 and B4 formed therein, which correspond with the respective connecting holes A1, A2, A3 and A4 of the first housing 12. Further, the manifold 70 has connecting holes C1, C2, C3 and C4, which correspond with the respective connecting holes A1, A2, A3 and A4 of the first housing 20, and also with the respective connecting holes B1, B2, B3 and B4 of the main housing 30. The first housing 20, the main housing 30 and the manifold 70 are connected with each other by using a plurality of fasteners F1, F2, F3 and F4 so as to arrange the first housing 20, the main housing 30 and the manifold 70 in series as shown in FIGS. 1, 4, and 6. For example, the respective connecting holes A1, B1 and C1 of the first housing 20, the main housing 30 and the manifold 70 are aligned, and the first housing 20, the main housing 30 and the manifold 70 are connected with each other by fastening the fastener F1. However, as discussed above, in another embodiment the first housing 20, the main housing 30 and the manifold 70 may be formed as one integrated unit.

Further, the first housing 20 has second connecting holes U1, U2 which correspond to second connecting holes V1, V2 of the main housing 30. The first housing 20 and the main housing 30 are additionally connected with each other by fastening the first housing 20 and the main housing 30 via second connecting holes U1, U2 of the first housing 20 with corresponding second connecting holes V1, V2 of the main housing 30 using second fasteners G1, G2, respectively.

FIG. 2 shows an exploded view of the vaporizer apparatus as viewed from right front top.

The first housing 20 may be a box-shaped housing as shown in FIGS. 1-5. However, the first housing 20 may be a cylindrical-shaped housing, a hexagonal-shaped housing or other suitable shaped housing.

The first housing 20 includes a battery chamber BC and is configured to receive a battery holder 21, a control unit 24 and a position-sensing device 28 (which may be a hall effect sensor or an activation switch or other a position-sensing device). The battery holder 21 is configured to receive a battery 22 including one or more battery cells **22*a* of suitable specification. The battery cells 22*a* may be connected in series or parallel if the plurality of battery cells 22*a* are used to achieve a desired power. The control unit 24 is mounted on the battery holder 21. The battery 22 is connected with each of the control unit 24 and the pump 80, and provides power thereto at a desired specification, e.g., at 3V. However, the control unit 24 and the pump 80 may receive a power from a different power source in addition to the battery 22 or separate from the battery 22**.

The first housing 20 further includes a top cover plate Tp and a bottom cover plate Bp. The top and bottom cover plates Tp, Bp are placed on top and bottom portions of the battery chamber BC, respectively. The top cover plate Tp is held in place on the top portion of battery chamber BC by using a plurality of fasteners Tf, and the bottom cover plate Bp is held in place on the bottom portion of the battery chamber BC by using a plurality of fasteners Bf.

The control unit 24 includes a circuit board 26. The hall effect sensor 28 is connected to the circuit board 26 and provides input signal to the circuit board 26 when the operation unit 50 is operated (discussed below) and position of the magnetic nut 64 is changed due to pressing of the knob 54. The hall effect sensor 28 measures the magnitude of a magnetic field of the magnetic nut 64. The hall effect sensor 28 and magnetic nut 64 are used to activate the control unit 24 but may be substituted with an activation switch or other mechanism.

The control unit 24 operates the pump 80 based on input received from the hall effect sensor 28 or an activation switch or other mechanism. The control unit 24 may be placed on a backside of the battery holder 21. The control unit 24 also provides a charging circuit for the batteries **22*a* as well as the modulation circuitry for the pump 80**.

The main housing 30 is a box-shaped unit. The main housing 30 is disposed between the first housing 20 and the manifold 70.

Figure 9:
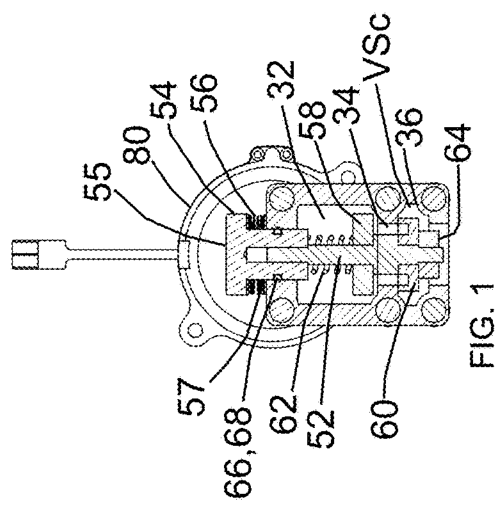
FIG. 9 is a cross-sectional view taken along line A-A in FIG. 8.

As it can be seen from FIG. 9, the main housing 30 has an oil chamber 32, an oil reservoir 34 and an evacuation chamber 36 formed therein. The oil reservoir 34 is formed between the oil chamber 32 and the evacuation chamber 36. In other words, the oil reservoir is an oil path between the oil chamber 32 and the evacuation chamber 36.

Further, main housing 30 has an oil-feeding hole 38 and a knob opening (also referred to as an operation unit opening) 40 formed therein. The oil-feeding hole 38 facilitates filling of oil in the oil chamber 32. A cap (not shown) is provided for selectively opening and closing the oil-feeding hole 38. The knob opening 40 is configured to receive the operation unit 50 therein for arranging the operation unit 50 into the main housing 30.

Furthermore, the main housing 30 has an outlet opening 42 formed therein. The outlet opening 42 is connected with the manifold 70, specifically with an inlet opening 76 of the manifold 70.

The operation unit 50 is disposed in the knob opening 40 formed in the main housing 30. The operation unit 50 is operable to seal a top of the oil reservoir 34 and also to seal a bottom of the evacuation chamber 36 thereby trapping oil in the oil reservoir 34 and the evacuation chamber 36 and further creating a vacuum sealed chamber Vsc.

The operation unit 50 includes a shaft 52, an operating knob (also referred to as a top button or a knob or an activation mechanism) 54 mounted on the shaft 52, a stacked disc spring (top spring) 56 disposed between the top portion 14 of the main housing 30 and the operating knob 54, a shaft spring 62 arranged on the shaft 52, specifically on a portion thereof is disposed in the oil chamber 32 between top seal 58 arranged at the mouth/top portion of the oil reservoir 34, which is a bottom or lower portion of the oil chamber 32, a bottom seal 60 disposed at a bottom portion of the evacuation chamber 36, and a magnetic nut 64 arranged below the bottom seal 60 on lower portion of the shaft 52. The stacked disc spring 56, the shaft spring 62, the top seal 58, the bottom seal 60 and the magnetic nut 64 are concentrically arranged along the shaft 52.

A rubber seal 66 including an O-ring 68 is disposed between the knob opening 40 of the main housing 30 and the operating knob 54. The operating knob 54 has an upper portion 55 and a lower portion 57. The top spring 56 which may be a stack disk spring is mounted between lower portion 57 of the operating knob 54 and an outer portion of the main housing 30.

The manifold (also referred to as an air flow chamber) 70 is a box-shaped unit. However, the manifold may be of a cylindrical shape.

The manifold 70 includes a first chamber 72, and a second chamber 74, which is separate from the first chamber 72.

The first chamber 72 is disposed next to the main housing 30. A first side wall **72*a* of the first chamber 72 has an inlet opening 76 formed therein. The inlet opening 76 of the first chamber 72 is connected with the outlet opening 42 of the main housing 30. A first top wall 72*b* of the first chamber 72 has one or more first connector openings 77 formed therein. The first connector opening 77 is configured to receive an inlet 82 (also referred to as a suction end pipe) of the piezo pump 80. The manifold 70 and the pump 80 may be combined into a single housing to reduce cost and part count. In other words, one or more pumps may be disposed in the manifold 70 such that manifold 70 and the pumps 80** forms one single unit.

The second chamber 74 includes a second side wall **74*a* having an outlet opening 78 formed therein. The outlet opening 78 is configured to receive an inlet opening 92 of the mouthpiece 90. Further, the second chamber 74 includes a second top wall 74*b* having one or more second connector openings 79 formed therein. The second connector opening 77 is configured to receive an outlet 84 (also referred to as a discharge end pipe) of the piezo pump 80**.

Figure 19:
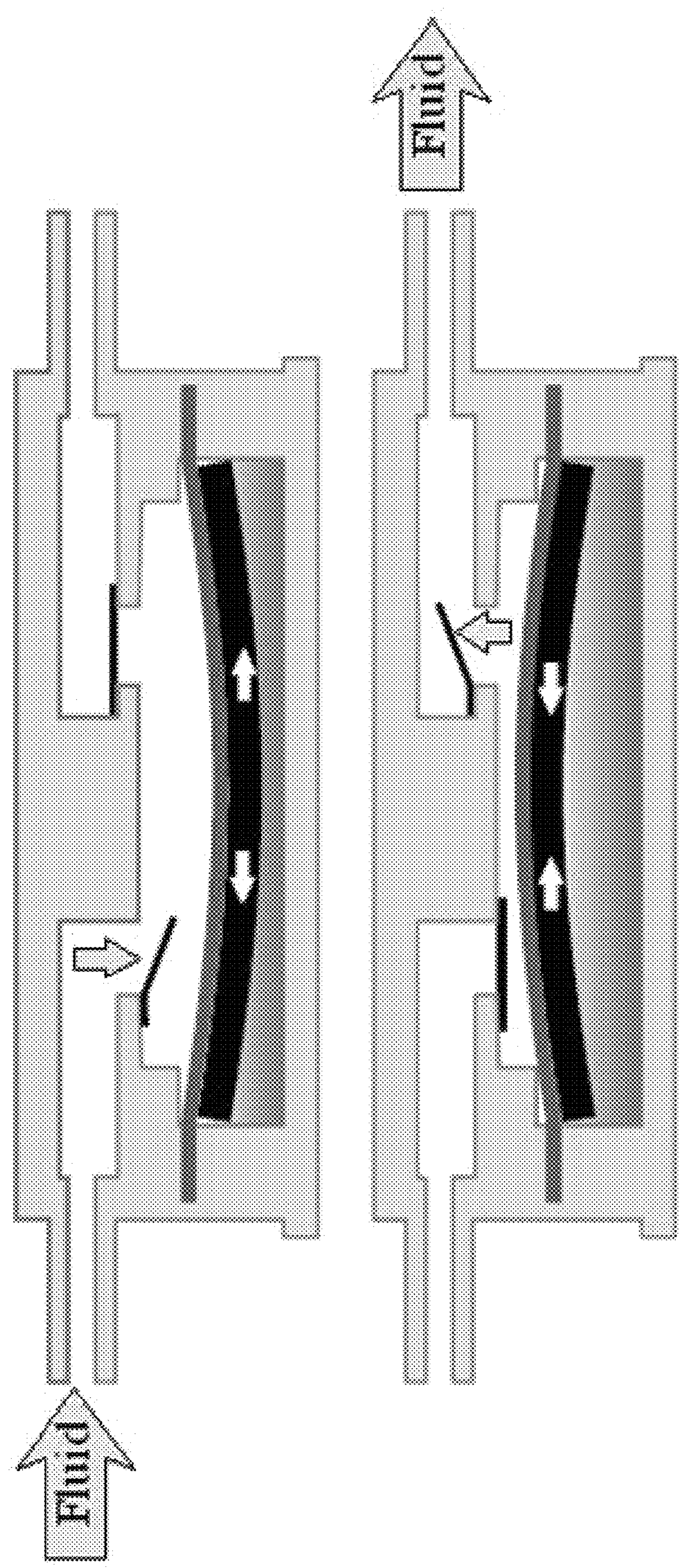
FIG. 19 is a schematic view of a piezo pump.

The pump 80 is a disc pump, which is a high-performance piezoelectric micropump operating through ultrasonic acoustic resonance. The disc pump can be applied to the pressure-driven flow of liquids. The pump 80 has compact form factor, i.e., it has high portability and it can be tightly integrated into portable devices such as the vaporizer apparatus of the present invention. A schematic of piezo pump is shown in FIG. 19.

The mouthpiece 90 is a cylindrical unit. The mouthpiece has an inlet opening 92 formed at one end thereof, and an outlet opening 94 formed at the other end thereof. The inlet opening 92 is connected to the outlet opening 78 of the second chamber 74 of the manifold 70.

The following is the description of operation of the vaporizer apparatus 10. The present invention works on the principle of gas law, for example, the ideal gas law. The ideal gas law is expressed by the following Equation (1).

$$PV=nRT \quad (1)$$

where,

P is the pressure

V is the volume n is the amount of substance of the gas (in moles)

R is the gas constant (0.08206 L·atm·K−1·mol−1)

T is the absolute temperature.

According to the present invention, upon operation of the operation unit 50, the top seal 58 isolates the oil reservoir 34 from the oil chamber 32 and the bottom seal 60 seals the bottom of the evacuation chamber 36, a vacuum seal is created which causes lowering of pressure for the oil trapped in the oil reservoir 34 and evacuation chamber 36. Further, when the piezo pump 80 is automatically triggered upon formation of the vacuum seal, i.e. turned on, the pressure differential is reduced to a value that causes oil that is trapped in the oil reservoir 34 and evacuation chamber 36 to vaporize and flow from the outlet opening 42 to the first chamber 72 then the second chamber 74 of manifold 70, and further to the mouthpiece 90.

In other words, when the operation unit 50 is operated, i.e., by pressing down the knob (top button) 54 thereof, the shaft 52 is pushed down along with the knob 54, until the top seal 58 (top rubber block) seals of the top of the oil reservoir 34 while trapping oil in the oil reservoir 34. The shaft spring 62 is then further compressed until the bottom seal (bottom rubber block) 60 seals the bottom of the evacuation chamber 36 thereby creating a vacuum seal. Once the vacuum seal is created, the magnetic nut 64 will have reached a point to trigger the hall effect sensor 28, which is operatively connected to the circuit board 26 of the control unit 24 that turns the piezo pump 80 on when hall effect sensor 28 is triggered. The piezo pump 80 is powered by the battery 22. Upon the turning the piezo pump 80 on, the pressure differential is greatly reduced, causing the oil that was trapped in the oil reservoir 34 and evacuation chamber 36 to vaporize and flow though the manifold (also referred to as an air flow chamber), out through the mouthpiece. A schematic diagram of a piezo pump is shown in FIG. 19.

The oil that was trapped in the oil reservoir 34 and evacuation chamber 36 is not heated or subjected to any heat source for vaporization thereof. Rather, the oil that was trapped in the oil reservoir 34 and evacuation chamber 36 is subjected to a very low pressure, for example, at 1007 mbar or below, for vaporization thereof.

Specifically, when the operation unit 50 is operated, the oil reservoir 34 and the evacuation chamber 36 are isolated from the oil chamber 32, thereby creating vacuum sealed chamber Vsc and displacement of the shaft 52 that also causes further displacement of the magnetic nut 64 that reaches a point of triggering the hall effect sensor 28 that provides signal to the control unit 24 to switch on the piezo pump 80, which further reduces the pressure differential, for example, at or below 1007 mbar, in the vacuum sealed chamber Vsc causing vaporization of the oil at or below a room temperature without subjecting the oil to a heat source, e.g., a heating element. The vapor thus produced is moved to a second chamber 74 of the manifold 70 and to the mouthpiece 90. The vapor in the mouthpiece 90 can be inhaled by the user through the outlet opening 94 of the mouthpiece 90.

In another embodiment, the mouthpiece may act as an activation mechanism for the operation unit. For example, when a user inhales through the mouthpiece, it may trigger the operation unit without the user pressing a knob to turn on the operation unit.

Since the oil is vaporized with no heat source and at or below a room temperature, vapor thus produced is at a low temperature that is not hot. Thus, the vaporizer apparatus 10 of the present invention cannot cause any heat related injury to a user. Moreover, since the oil is not heated or is not subjected to a heat source of any kind, the alteration of composition of the oil due to heat can be prevented.

Second Embodiment

A vaporizer apparatus 10 according a second embodiment of the present invention is shown in FIGS. 10-18.

Figure 10:
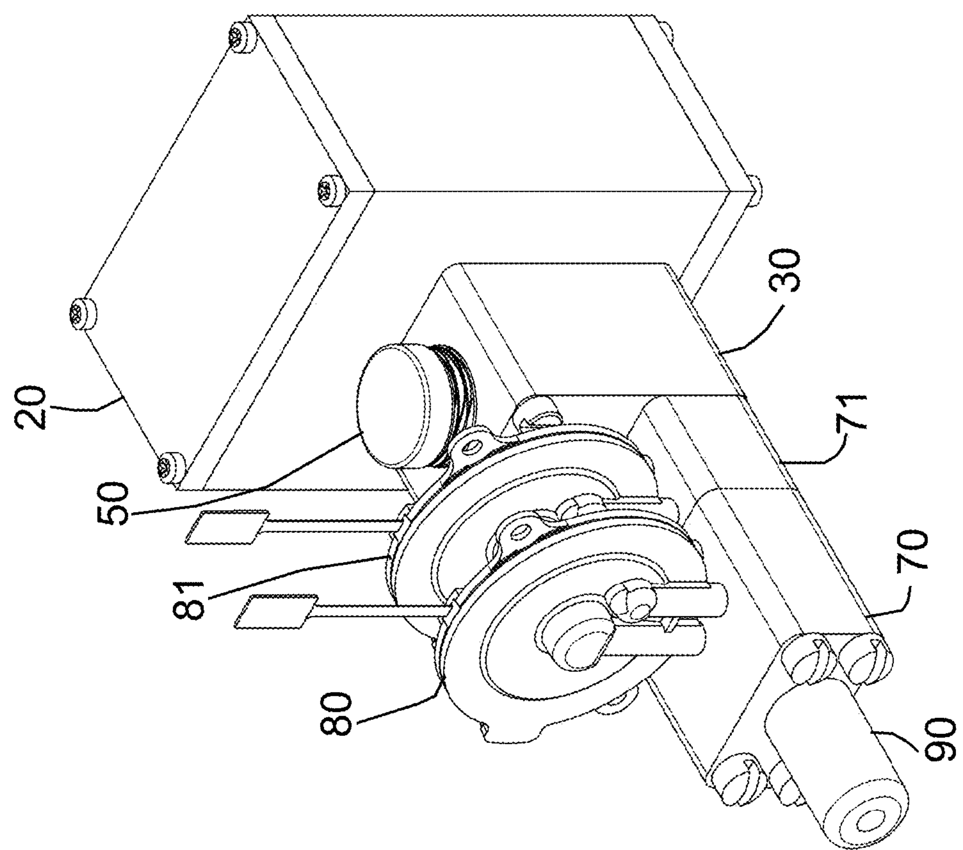
FIG. 10 shows a perspective view of a vaporizer apparatus as viewed from right front top according to a second embodiment of the present invention.
Figure 11:
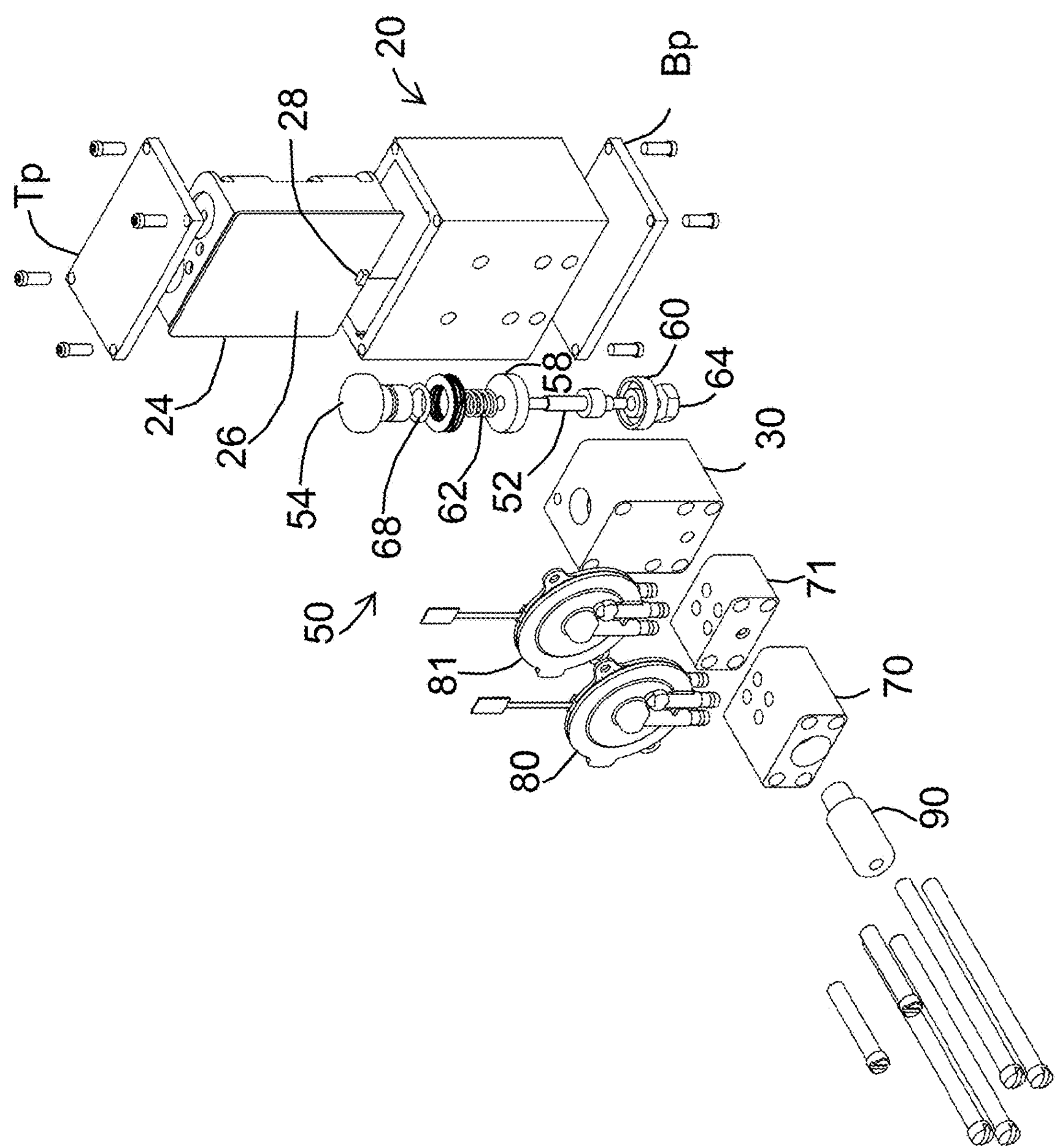
FIG. 11 shows an exploded view of the vaporizer apparatus as viewed from right front top according to the second embodiment.
Figure 12:
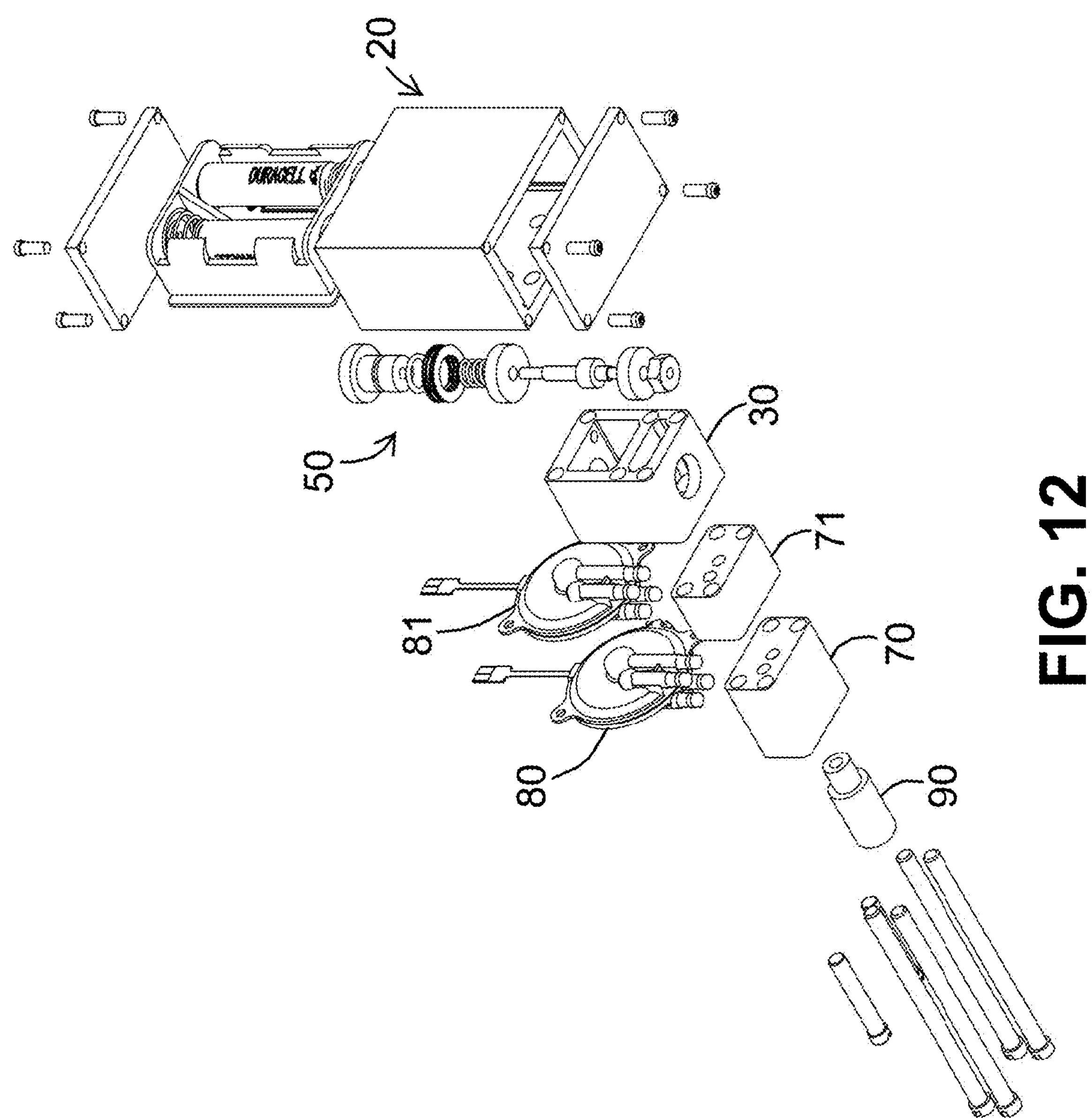
FIG. 12 shows another exploded view of the vaporizer apparatus as viewed from right back bottom according to the second embodiment.
Figure 13:
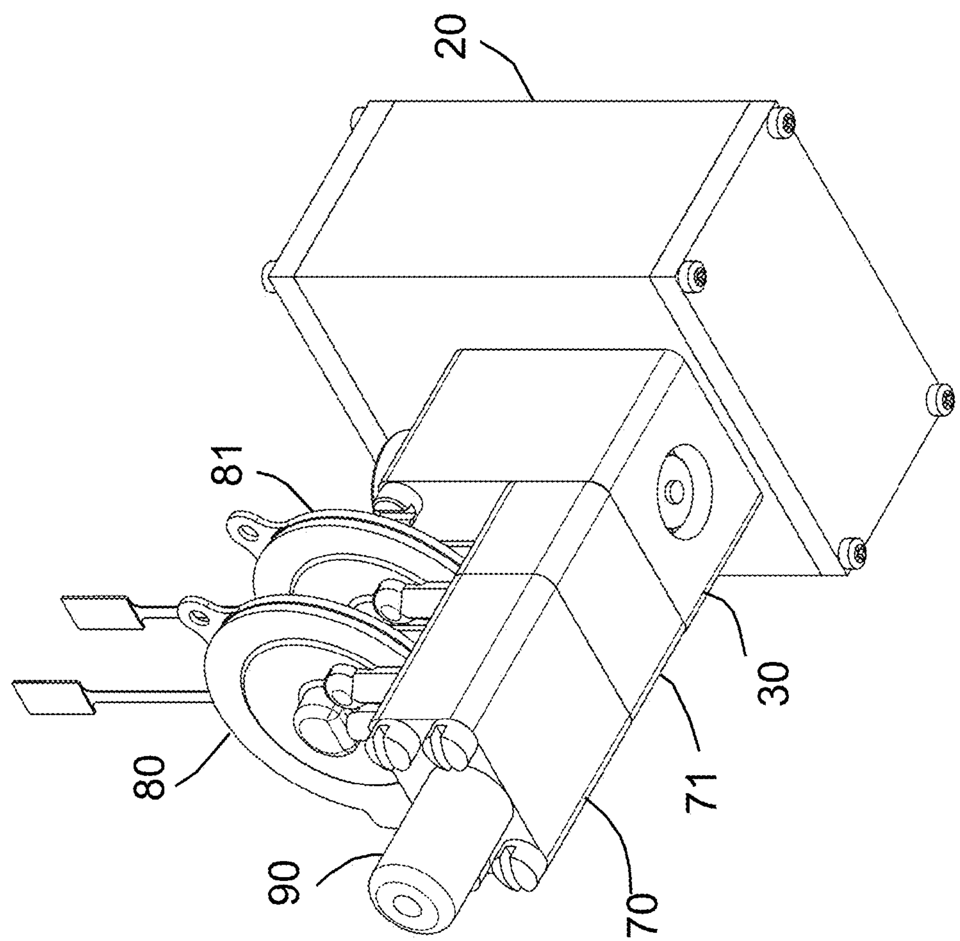
FIG. 13 shows a perspective view of the vaporizer apparatus as viewed from right front bottom according to the second embodiment.
Figure 14:
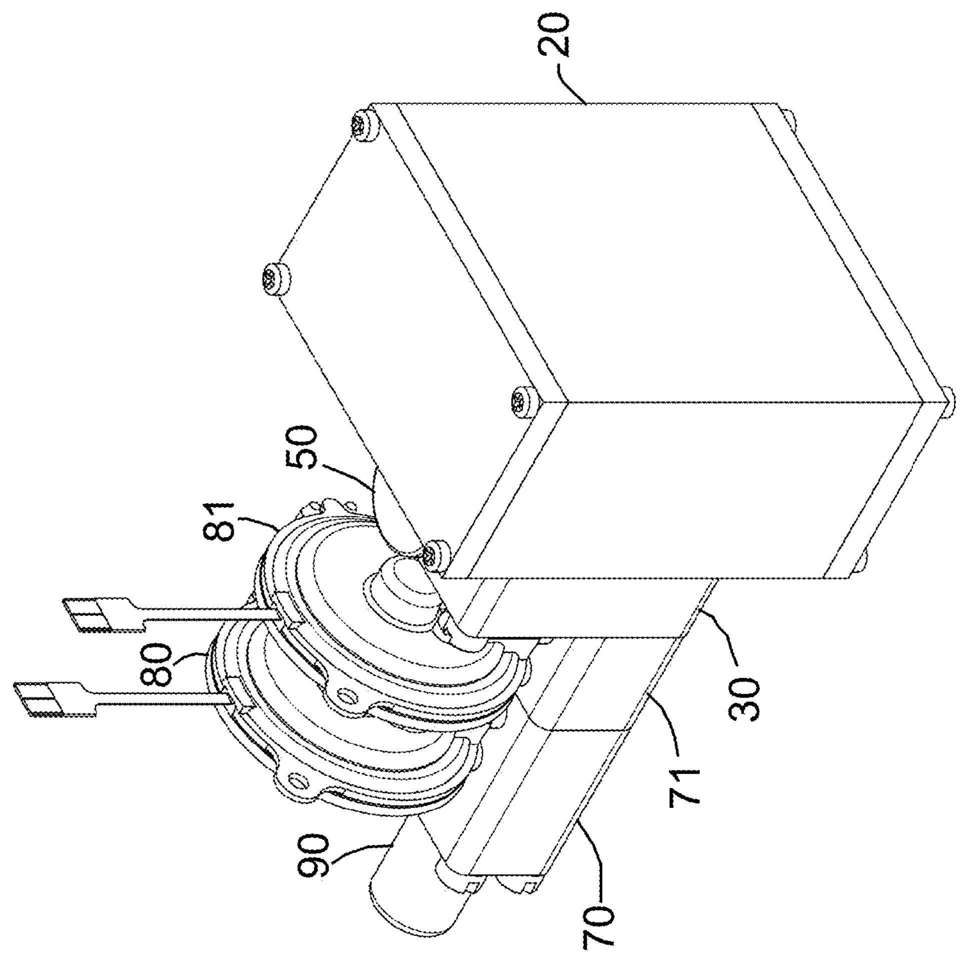
FIG. 14 shows a perspective view of the vaporizer apparatus as viewed from right back top according to the second embodiment.
Figure 15:
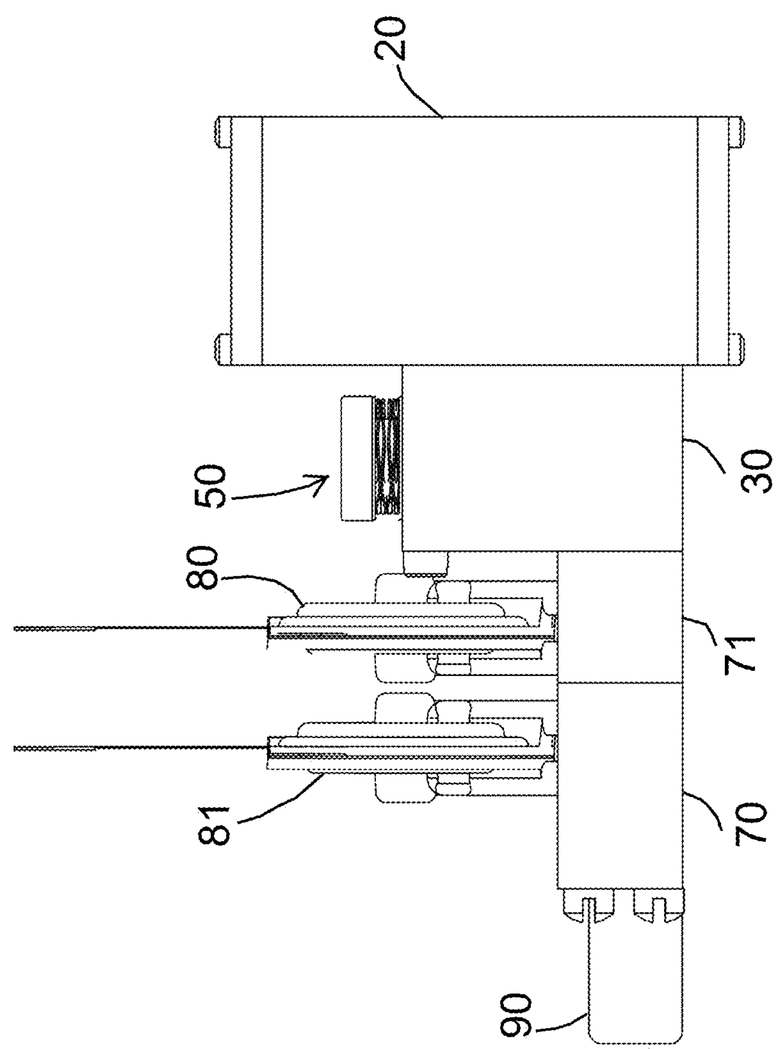
FIG. 15 shows a right side view of the vaporizer apparatus according to the second embodiment.
Figure 16:
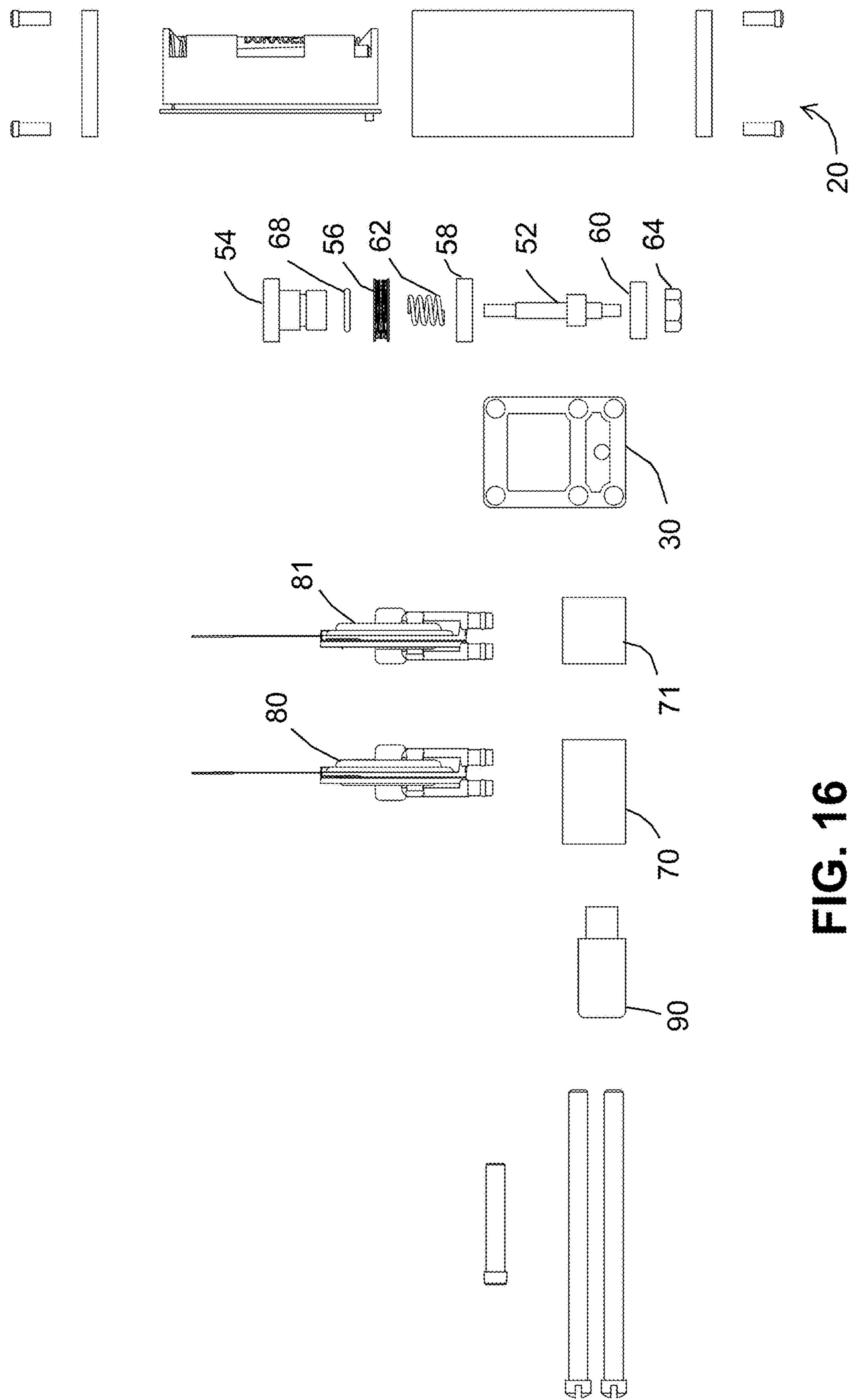
FIG. 16 shows an exploded view of the vaporizer apparatus as viewed right side according to the second embodiment.
Figure 17:
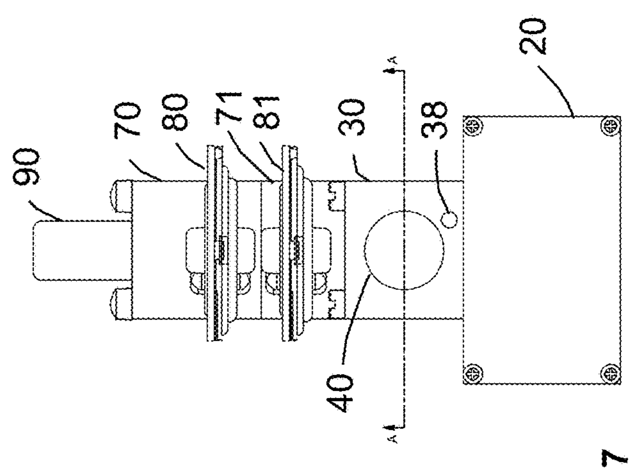
FIG. 17 is a sectional view of the vaporizer apparatus according to the second embodiment.
Figure 18:
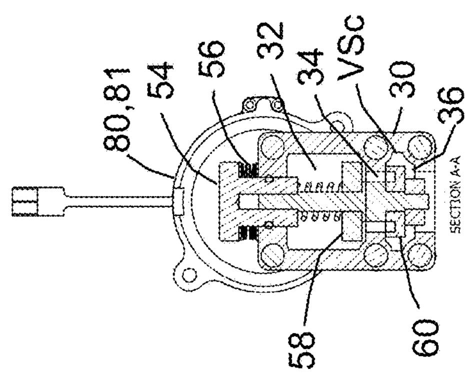
FIG. 18 is a cross-sectional view taken along line A-A in FIG. 17.

FIG. 10 shows a perspective view of a vaporizer apparatus as viewed from right front top according to the second embodiment. FIGS. 11 and 12 show exploded views as viewed from right front top and right back bottom, respectively. FIGS. 13 and 14 show perspective views as viewed from right front bottom and right back top, respectively. FIGS. 15 and 16 show a right side view and exploded right side view, respectively. FIGS. 17-18 show various sectional views according to the second embodiment of the present invention.

It can be seen from FIGS. 10-20, the second embodiment of the present invention, is different from the first embodiment in that the second embodiment includes two piezo pumps—a first piezo pump 80 (which is similar to the piezo pump 80 of first embodiment) and a second piezo pump 81, and two manifolds—a first manifold 70 (which is similar to the manifold 70 of first embodiment) and a second manifold 71 on which the second piezo pump 81 is mounted. The second manifold 71 is arranged between the first manifold 70 and the main housing 30. Additional piezo pumps and manifolds may be included such that there are at least two piezo pumps and two manifolds. Alternately, a plurality of pumps may be mounted in one manifold.

The second manifold 71 has an inlet portion connected with main housing, specifically oil outlet thereof, and an outlet portion, which is connected with the inlet portion of the manifold such that the two piezo pumps 80 and 81 are arranged in series. However, piezo pumps 80, 81, which may be more than two, may be arranged in different combination. Further, the piezo pumps may have similar or different specifications.

The vaporizer apparatus 10 of the second embodiment is operated in a similar manner as the vaporizer apparatus 10 of the first embodiment with exception that both the piezo pumps 80 and 81 are activated when the operation unit 50 is operated.

Although the present invention has been described herein with respect to several specific illustrative embodiments, the foregoing description is intended to illustrate, rather than to limit the invention. Those skilled in the art of vaporizers will realize that many modifications of the illustrative embodiment can be made and would be operable. All such modifications, which are within the scope of the claims, are intended to be within the scope and spirit of the present invention.

What is claimed is:

1. A vaporizer apparatus comprising a main house having an oil chamber, an oil reservoir connected to the oil chamber, and an evacuation chamber connected to the oil reservoir formed therein;

an operation unit mounted onto the main housing;

a manifold connected to the main housing;

a pump mounted on the manifold;

a control unit connected to the operation unit and the pump;

wherein when said operation unit is operated, the oil reservoir is isolated from the oil chamber and a bottom of the evacuation chamber is sealed thereby creating a vacuum sealed chamber having oil trapped therein and being connected with an inlet of the pump, and the control unit turns the pump on causing a pressure differential so that the oil trapped in the vacuum sealed chamber vaporizes without heat and flows though the manifold.

2. The vaporizer apparatus according to claim 1, wherein said operation unit comprises a top seal arranged at a top portion of the oil reservoir and a bottom seal arranged at a bottom portion of the evacuation chamber.

3. The vaporizer apparatus according to claim 1, wherein said operation unit comprises a shaft and a nut mounted at one end portion of the shaft.

4. The vaporizer apparatus according to claim 3, wherein said control unit comprises one of a hall effect sensor, an activation switch or a position sensing device connected to the nut.

5. The vaporizer apparatus according to claim 1, wherein said operation unit comprises a shaft, a knob mounted on one end portion of the shaft;

a top seal arranged a top portion of the oil reservoir;

a shaft spring mounted on the shaft between the knob and the top seal;

a bottom seal arranged at a bottom portion of the evacuation chamber;

wherein when said knob is pressed, the shaft spring acts on the top seal which seals a top of oil reservoir, and a portion of the shaft acts on the bottom seal which seals bottom of the evacuation chamber.

6. The vaporizer apparatus according to claim 1, wherein said pump is a piezoelectric micro pump.

7. The vaporizer apparatus according to claim 1, further comprising a mouthpiece connected to said manifold.

8. The vaporizer apparatus according to claim 1, wherein said power source is a battery.

9. A vaporizer apparatus comprising a main house having an oil chamber, an oil reservoir connected to the oil chamber, and an evacuation chamber connected to the oil reservoir formed therein;

an operation unit mounted onto the main housing;

at least two manifolds comprising a first manifold connected to the main housing, and a second manifold connected to the first manifold;

at least two pumps comprising a first pump mounted on the first manifold, and a second pump mounted on the second manifold;

a control unit connected to the operation unit and said at least two pumps;

wherein when said operation unit is operated, the oil reservoir is isolated from the oil chamber and a bottom of the evacuation chamber is sealed thereby creating a vacuum sealed chamber having oil trapped therein and being connected with an inlet of the pump, and the control unit turns said at least two pumps on causing a pressure differential so that the oil trapped in the vacuum sealed chamber vaporizes without heat and flows though the manifold.

10. The vaporizer apparatus according to claim 9, wherein said operation unit comprises a top seal arranged at a top portion of the oil reservoir and a bottom seal arranged at a bottom portion of the evacuation chamber.

11. The vaporizer apparatus according to claim 9, wherein said operation unit comprises a shaft and a nut mounted at one end portion of the shaft.

12. The vaporizer apparatus according to claim 11, wherein said control unit comprises one of a hall effect sensor, an activation switch and a position sensing device connected to the nut.

13. The vaporizer apparatus according to claim 9, wherein said operation unit comprises a shaft, a knob mounted on one end portion of the shaft;

a top seal arranged a top portion of the oil reservoir;

a shaft spring mounted on the shaft between the knob and the top seal;

a bottom seal arranged at a bottom portion of the evacuation chamber;

wherein when said knob is pressed the shaft spring acts on the top seal which seals a top of oil reservoir, and a portion of the shaft acts on the bottom seal which seals bottom of the evacuation chamber.

14. The vaporizer apparatus according to claim 9, wherein each of said pumps is a piezoelectric micro pump.

15. A vaporizer apparatus comprising a first housing comprising a power source;

a main housing connected to the first housing, and having an oil chamber, an oil reservoir connected to the oil chamber, and an evacuation chamber connected to the oil reservoir formed therein;

an operation unit mounted onto the main housing;

a manifold connected to the main housing, and having a pump disposed therein; and a control unit connected to the operation unit and the pump;

said control unit and the pump being connected to the power source;

a mouthpiece connected to the manifold;

wherein when said operation unit is operated, the oil reservoir is isolated from the oil chamber and a bottom of the evacuation chamber is sealed thereby creating a vacuum sealed chamber having oil trapped therein and being connected with an inlet of the pump, and the control unit turns the pump on causing a pressure differential so that the oil trapped in the vacuum sealed chamber vaporizes without heat and flows though the manifold and the mouthpiece.

16. The vaporizer apparatus according to claim 15, wherein said operation unit comprises a top seal arranged at a top portion of the oil reservoir and a bottom seal arranged at a bottom portion of the evacuation chamber.

17. The vaporizer apparatus according to claim 15, wherein said operation unit comprises a shaft and a nut mounted at one end portion of the shaft.

18. The vaporizer apparatus according to claim 17, wherein said control unit comprises one of a hall effect sensor, an activation switch, and a position sensing device connected to the nut.

19. The vaporizer apparatus according to claim 15, wherein said operation unit comprises a shaft, a knob mounted on one end portion of the shaft;

a top seal arranged a top portion of the oil reservoir;

a shaft spring mounted on the shaft between the knob and the top seal;

a bottom seal arranged at a bottom portion of the evacuation chamber;

wherein when said knob is pressed, the shaft spring acts on the top seal which seals a top of oil reservoir, and a portion of the shaft acts on the bottom seal which seals bottom of the evacuation chamber.

20. The vaporizer apparatus according to claim 15, wherein said pump is a piezoelectric micro pump.

* * * * *